(12) United States Patent
Sugimoto et al.

(10) Patent No.: US 8,740,965 B2
(45) Date of Patent: Jun. 3, 2014

(54) STENT DELIVERY SYSTEM

(75) Inventors: Ryota Sugimoto, Kanagawa (JP);
Takashi Kitaoka, Kanagawa (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 141 days.

(21) Appl. No.: 13/416,691

(22) Filed: Mar. 9, 2012

(65) Prior Publication Data

US 2012/0172969 A1 Jul. 5, 2012

Related U.S. Application Data

(63) Continuation of application No. PCT/JP2010/065638, filed on Sep. 10, 2010.

(30) Foreign Application Priority Data

Sep. 16, 2009 (JP) ................................. 2009-214985

(51) Int. Cl.
*A61F 2/82* (2013.01)

(52) U.S. Cl.
USPC ........................................ 623/1.12

(58) Field of Classification Search
USPC ................... 606/108; 623/1.11, 1.12, 1.23
See application file for complete search history.

(56) References Cited

U.S. PATENT DOCUMENTS

| | | | | |
|---|---|---|---|---|
| 5,026,377 A | * | 6/1991 | Burton et al. | 606/108 |
| 5,480,423 A | * | 1/1996 | Ravenscroft et al. | 623/1.11 |
| 5,484,444 A | * | 1/1996 | Braunschweiler et al. | 623/1.11 |
| 5,603,698 A | * | 2/1997 | Roberts et al. | 604/104 |
| 5,645,559 A | * | 7/1997 | Hachtman et al. | 623/1.2 |
| 5,702,418 A | * | 12/1997 | Ravenscroft | 623/1.11 |
| 5,776,141 A | * | 7/1998 | Klein et al. | 623/1.11 |
| 5,817,102 A | * | 10/1998 | Johnson et al. | 606/108 |
| 5,824,058 A | * | 10/1998 | Ravenscroft et al. | 623/1.11 |
| 5,984,964 A | * | 11/1999 | Roberts et al. | 623/1.11 |
| 6,120,522 A | * | 9/2000 | Vrba et al. | 606/190 |
| 6,126,685 A | * | 10/2000 | Lenker et al. | 623/1.11 |
| 6,136,006 A | * | 10/2000 | Johnson et al. | 606/108 |
| 6,168,617 B1 | * | 1/2001 | Blaeser et al. | 623/1.11 |

(Continued)

FOREIGN PATENT DOCUMENTS

| | | |
|---|---|---|
| JP | 4-25755 U | 2/1992 |
| JP | 11-505441 A | 5/1999 |

(Continued)

OTHER PUBLICATIONS

International Search Report (PCT/ISA/210) issued on Oct. 19, 2010, by Japanese Patent Office as the International Searching Authority for International Application No. PCT/JP2010/065638.

*Primary Examiner* — Ryan Severson

(74) *Attorney, Agent, or Firm* — Buchanan Ingersoll & Rooney P.C.

(57) ABSTRACT

A stent delivery system includes a self-expanding stent, an inner tube body which has a guide wire lumen, and a sheath which has the stent contained within the tip section thereof. The stent can be discharged by moving the sheath to the base end side relative to the inner tube body. The inner tube body is provided at a position within the base end section of the stent and is provided with an elastic member for pressing the stent in the direction to the sheath. The stent is gripped by the elastic member and the sheath and is adapted to be slidable relative to the sheath.

18 Claims, 11 Drawing Sheets

(56) References Cited

U.S. PATENT DOCUMENTS

| | | | |
|---|---|---|---|
| 6,187,013 B1 * | 2/2001 | Stoltze et al. | 606/108 |
| 6,203,558 B1 * | 3/2001 | Dusbabek et al. | 606/198 |
| 6,241,758 B1 * | 6/2001 | Cox | 623/1.11 |
| 6,251,132 B1 * | 6/2001 | Ravenscroft et al. | 623/1.11 |
| 6,306,162 B1 * | 10/2001 | Patel | 623/1.11 |
| 6,554,848 B2 * | 4/2003 | Boylan et al. | 606/191 |
| 6,582,460 B1 * | 6/2003 | Cryer | 623/1.11 |
| 6,607,551 B1 * | 8/2003 | Sullivan et al. | 623/1.11 |
| 6,656,212 B2 * | 12/2003 | Ravenscroft et al. | 623/1.11 |
| 6,699,274 B2 * | 3/2004 | Stinson | 623/1.12 |
| 6,833,003 B2 * | 12/2004 | Jones et al. | 623/1.11 |
| 6,991,646 B2 * | 1/2006 | Clerc et al. | 623/1.11 |
| 7,105,014 B2 * | 9/2006 | Murray, III | 623/1.11 |
| 7,115,140 B2 * | 10/2006 | Stoltze et al. | 623/1.11 |
| 7,470,282 B2 * | 12/2008 | Shelso | 623/1.12 |
| 7,473,271 B2 * | 1/2009 | Gunderson | 623/1.12 |
| 7,517,361 B1 * | 4/2009 | Ravenscroft | 623/1.12 |
| 7,651,525 B2 * | 1/2010 | Dolan | 623/1.2 |
| 7,655,031 B2 * | 2/2010 | Tenne et al. | 623/1.11 |
| 7,717,949 B2 * | 5/2010 | Dorn | 623/1.11 |
| 7,799,266 B2 * | 9/2010 | Parker et al. | 264/573 |
| 7,815,669 B2 * | 10/2010 | Matsuoka et al. | 623/1.11 |
| 7,867,267 B2 * | 1/2011 | Sullivan et al. | 623/1.11 |
| 7,935,140 B2 * | 5/2011 | Griffin | 623/1.11 |
| 8,057,527 B2 * | 11/2011 | Jordan et al. | 623/1.11 |
| 8,172,891 B2 * | 5/2012 | Shelso | 623/1.11 |
| 8,287,582 B2 * | 10/2012 | Dorn | 623/1.11 |
| 2004/0106977 A1 * | 6/2004 | Sullivan et al. | 623/1.12 |
| 2004/0204749 A1 * | 10/2004 | Gunderson | 623/1.12 |
| 2006/0030922 A1 * | 2/2006 | Dolan | 623/1.11 |
| 2006/0184225 A1 * | 8/2006 | Pryor | 623/1.11 |
| 2006/0259124 A1 * | 11/2006 | Matsuoka et al. | 623/1.12 |
| 2007/0100421 A1 * | 5/2007 | Griffin | 623/1.11 |
| 2008/0009934 A1 * | 1/2008 | Schneider et al. | 623/1.11 |
| 2008/0039920 A1 * | 2/2008 | Peacock et al. | 623/1.11 |

FOREIGN PATENT DOCUMENTS

| | | |
|---|---|---|
| JP | 2007-097620 A | 4/2007 |
| JP | 2008-508936 A | 3/2008 |
| WO | WO 96/26689 A1 | 9/1996 |

* cited by examiner

STENT DELIVERY SYSTEM

This application is a continuation of International Application No. PCT/JP2010/065638 filed on Sep. 10, 2010, and claims priority to Japanese Application No. 2009-214985 filed on Sep. 16, 2009, the entire content of both of which is incorporated herein by reference.

TECHNICAL FIELD

The present invention generally relates to a stent delivery system to be used for improving a stenosed part or occluded part in a living body lumen such as blood vessel, bile duct, trachea, esophagus, urethra, etc.

BACKGROUND DISCUSSION

A stent is a generally tubular medical device which, for treatment of various diseases arising from stenosis or occlusion of a blood vessel or other living body lumen, is indwelled in the stenosed or occluded part to dilate the part and secure the lumen (i.e., keep the lumen in an open state).

The following describes an example in which the stent is used in a blood vessel. The stent is a body which, for insertion from the outside into the inside of a living body, is small in diameter at the time of insertion, and is expanded at the target stenosed or occluded part so as to be enlarged in diameter and to maintain the lumen as it is (i.e., in an open state).

In general, stents are hollow cylindrical bodies obtained by processing metallic wires or a metallic pipe. A stent is mounted to a catheter or the like in a radially reduced state, is inserted into a living body, and is expanded in a target part by some method, to be fixed in close contact with the inner wall of the lumen at the target part, thereby maintaining the lumen in an open state. The stents are classified by function and placement method into self-expandable stents and balloon-expandable stents. A balloon-expandable stent is a stent which itself does not have an expanding function. The balloon-expandable stent is used in a method in which the stent mounted on a balloon is inserted into a target part, and thereafter the balloon is dilated to expand (plastically deform) the stent by the dilation force of the balloon, thereby fixing the stent in close contact with the inner surface of the target lumen. This type of stent requires the stent-expanding operation as described above. On the other hand, a self-expanding stent is a stent which itself is provided with an expanding function. The self-expanding stent is used in a method in which the stent contained in a radially contracted state within a stent-containing tube body is inserted into a living body, and is discharged from the stent-containing tube body at a target part so as to automatically return into its original expanded state, thereby being fixed in close contact with the inner wall of the lumen at the target part and maintaining the lumen shape in an open state.

The purpose of the placement of a stent at present is to return a blood vessel stenosed for some reason to its original open state. In most cases, the stents are mainly for preventing or reducing the risk or extent of restenosis which might occur after such a procedure as PTCA. In recent years, to suppress the probability of restenosis more assuredly, drug-eluting stents with a drug such as immunosuppressor or carcinostatic loaded on the stent are also used, and the effect is generally known.

Most of the self-expanding stents are used in peripheral regions such as blood vessels of inferior limb and carotid arteries. An example is disclosed in International Application Publication No. WO 96/26689 (JP-T-H11-505441.

In this known system, the self-expandable stent is contained in a stent-containing tube body in a stent delivery system. Due to the self-expanding property of the stent, the positioning of the stent at the time of placement is difficult as compared with the case of a balloon-expandable stent. In addition, a jumping phenomenon may occur in which the stent jumps out of the stent-containing tube body unguardedly. If this phenomenon occurs, the stent would be disposed at a position deviated from the planned position. It may in some cases be necessary to readjust the placement position after the stent is exposed to a certain extent from the stent-containing tube body during the stent placement procedure. In the case of the known system, however, it is difficult to re-contain the stent into the stent-containing tube body (i.e., to once again load the stent in the stent-containing tube body).

SUMMARY

According to one aspect, the stent delivery system disclosed here includes: a stent having a hollow shape, compressed toward a center axis of the stent during insertion into a living body, and restorable to its pre-compression shape by expanding outward when indwelled in the living body; an inner tube body having a guide wire lumen configured to receive a guide to assist guiding movement of the stent delivery system in the living body; a stent-containing tube body having a distal portion containing the stent, the stent covering a distal portion of the inner tube body, the stent being dischargeable from the stent-containing tube body by moving the stent-containing tube body proximally relative to the inner tube body; the inner tube body including an elastic member disposed at a position at least within a proximal portion of the stent and pressing the stent in a direction toward the stent-containing tube body; and the stent is clamped between the elastic member and the stent-containing tube body, and is slidable relative to the stent-containing tube body.

The stent delivery system inhibits or prevents unguarded jumping-out of the stent, as a result of the self-expanding property of the stent, when discharging the stent from the stent-containing tube body, and the stent can be re-contained into the stent-containing tube body even after the stent is exposed to a certain extent from the stent-containing tube body. More specifically, the stent is clamped (gripped) between the elastic member and the stent-containing tube body, so that the stent is not susceptible to jumping out of the stent-containing tube body in an unguarded manner as would otherwise be the case. In addition, if only a part of the stent remains clamped between the elastic member and the stent-containing tube body, it is possible, even after the stent is partly exposed from the stent-containing tube body, to re-contain the exposed part of the stent into the stent-containing tube body by a holding force at the clamping (gripping) portion. In this case, therefore, the placement position of the stent can be corrected, and the stent can be placed at a target part in a reliable manner.

The stent has a distal portion extending toward a distal end of the stent-containing tube body and a proximal portion extending toward a proximal end of the stent-containing tube body, and the stent does not have any bent portion which protrudes toward the proximal end and is unconnected to another strut of the stent, other than the proximal portion. By moving the stent-containing tube body distally relative to the inner tube body after exposing a distal end portion of the stent from the stent-containing tube body, the exposed portion of the stent is once again positionable in the stent-containing tube body.

The elastic member can be in the form of a wire coil comprised of a fixation section fixing the elastic member to the inner tube body and an elastic section which presses the stent. The elastic section is preferably deformable and is configured to incline in a proximal direction when pulling the stent-containing tube body to move proximally relative to the inner tube body, and to incline in a distal direction when pushing the stent-containing tube body to move distally relative to the inner tube body. At least the elastic section of the wire coil is inclined in a proximal direction or in a distal direction.

Preferably, a plurality of the elastic members are fixed to the inner tube body. The elastic members can be positioned to press against the stent in a region ranging from a central portion of the stent to the proximal portion of the stent, with no elastic members pressing against the stent in a region ranging from the central portion of the stent to a distal end of the stent. The elastic members can alternatively be positioned in an area ranging from a distal portion of the stent to the proximal portion of the stent.

The elastic member is preferably configured to press at least a part of an inner surface of the stent by contacting the inner surface of the stent.

When the stent delivery system includes a plurality of the elastic members, the elastic members are preferably spaced apart from one another, and press at least a part of an inner surface of the stent by contacting the inner surface of the stent. In one possibility, the parts of the stent pressed by the elastic members are arranged substantially rectilinearly along an axial direction of the stent. In another possibility, the parts of the stent which are pressed by adjacent ones of the elastic members are different as viewed along an axial direction of the stent. Still further, the elastic member can be arranged such the parts of the stent which are pressed by the elastic members are arranged zigzag along an axial direction of the stent.

The elastic member can be a wire coil comprising: a starting end fixation section fixed to the inner tube body and an opposite end either fixed to the inner tube body or forming a free end; and a spirally shaped stent-pressing elastic section between the starting end fixation section and the opposite end, with the spirally shaped stent-pressing elastic section extending over a predetermined length along an axial direction of the stent.

According to another possibility, the elastic member includes: a starting end fixation section fixed to the inner tube body and an opposite end either fixed to the inner tube body or forming a free end; and a leaf spring-configured stent-pressing elastic section between the starting end fixation section and the opposite end, the leaf spring-configured stent-pressing elastic section extending over a predetermined length along an axial direction of the stent and projecting at a central portion of the leaf spring-configured stent-pressing elastic section.

The inner tube body preferably comprises a distal-side tube having the guide wire lumen, and an inner tube main body having a distal portion fixed to a proximal end of the distal-side tube.

In accordance with another aspect disclosed here, a stent delivery system comprises: an inner tube body having a guide wire lumen configured to receive a guide wire to guide movement of the stent delivery system; a stent-containing tube body surrounding a distal portion of the inner tube body so that a space exists between an outer surface of the inner tube body and an inner surface of the stent-containing tube body; and a hollow longitudinally extending stent positioned in the space between the outer surface of the inner tube body and the inner surface of the stent-containing tube body so that the inner tube body passes through the stent. The stent is compressed while positioned in the space and is automatically expandable outwardly when exposed outside the stent-containing tube body. The stent possesses an inner surface, an proximal-most end and a distal-most end. An elastic member is positioned in the space between the outer surface of the inner tube body and the inner surface of the stent-containing tube body, and the elastic member contacts the inner surface of the stent only at a portion of the longitudinal extent of the stent so that the stent is clamped between the elastic member and the stent-containing tube body. The portion of the stent contacted by elastic member is located closer to the proximal-most end of the stent than the distal-most end of the stent. The stent-containing tube body is slidable proximally relative to the stent to expose the stent outside the stent-containing tube body and permit the stent to expand outwardly.

DETAILED DESCRIPTION

Figure 1:
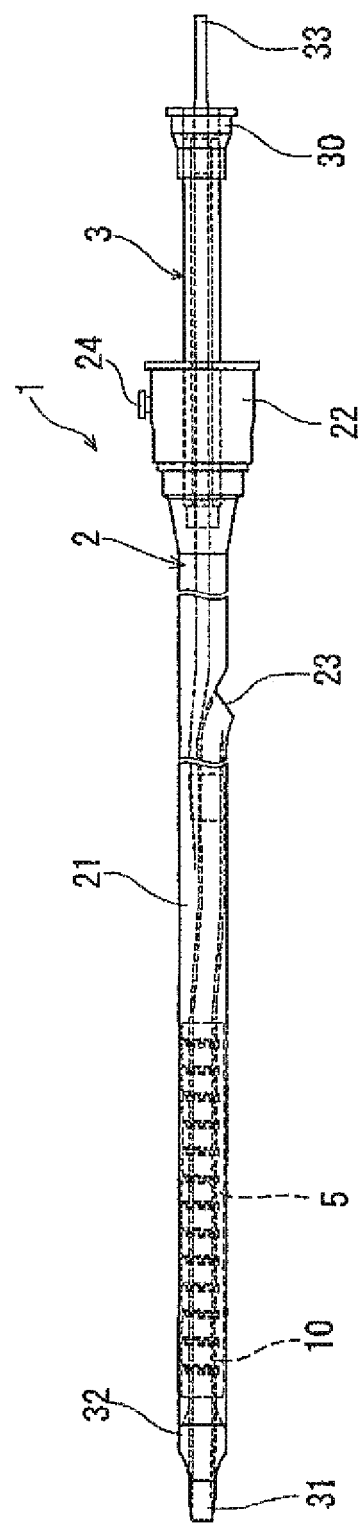
FIG. 1 is a side view of a stent delivery system according to one embodiment disclosed by way of example here.

The stent delivery system 1 disclosed here, constituting a sort of living organ lesion improving instrument, includes: a stent 10 possessing a substantially hollow cylindrical shape, compressed radially inwardly in the direction toward its center axis at the time of insertion into a living body, and capable of being restored to its pre-compression shape by expanding outward when indwelled in the living body; an inner tube body (shaft section) 3 having a guide wire lumen 61; and a stent-containing tube body (sheath) 2 having a distal portion which possesses or contains the stent 10. The stent 10 is disposed to cover a distal portion of the inner tube body 3, and is dischargeable by moving the stent-containing tube body 2 proximally relative to the inner tube body 3. In addition, the inner tube body 3 is provided with an elastic member 5 disposed at a position at least within a proximal portion of the stent to press the stent 10 in a direction toward the stent-containing tube body 2. The stent 10 is positioned and clamped between the elastic member 5 and the stent-containing tube body 2, and is adapted to be slidable relative to the stent-containing tube body 2. The stent 10 is not substantially slidable relative to the elastic member 5.

In the stent delivery system 1 according to the embodiment shown in the drawings, the inner tube body is a shaft section 3, and the stent-containing tube body is a sheath 2. The stent delivery system 1 according to this embodiment is thus constructed to include the stent 10 possessing a substantially hollow cylindrical shape, compressed in a direction toward its center axis at the time of insertion into a living body and capable of being restored to its pre-compression shape by expanding outward when indwelled in the living body; the shaft section 3 having the guide wire lumen 61; and the sheath 2 configured so that the stent 10 is contained in a distal portion of the sheath and covers a distal portion of the shaft section 3.

In addition, the stent 10 used in the stent delivery system 1 according to the embodiment shown in the drawings is configured to be restored to its pre-compression shape by expanding outward when indwelled in the living body, the stent-containing tube body (sheath) 2 is configured to contain or possess the automatically outwardly expandable stent 10 in a distal portion of the stent-containing tube body (sheath), and the shaft section 3 is configured to be inserted and passed slidably within the stent-containing tube body (sheath) 2 and to discharge the stent 10 from the distal end of the stent-containing tube body (sheath) 2. The stent 10 has a distal portion extending toward the distal end of the stent-containing tube body (sheath) 2, and a proximal portion extending toward the proximal end of the stent-containing tube body (sheath) 2. The stent 10 is configured so that, except for the proximal portion, there are no bent free ends that protrude toward the proximal end. That is, other than the proximal portion, the stent does not include portions, extending toward the proximal end, which are both bent and unconnected to another portion (another strut) of the stent. By moving the stent-containing tube body (sheath) 2 distally relative to the inner tube body (shaft section) 3 after exposing a distal-side portion of the stent from the stent-containing tube body (sheath) 2, the exposed portion can be re-contained into the stent-containing tube body (sheath) 2. The stent delivery system 1 also includes a guide wire lumen 61 having one end opening at the distal end of the stent delivery system and the other end opening on the proximal side relative to a stent-containing part of the sheath 2.

As shown in FIGS. 1 to 9, the sheath (stent-containing tube body) 2 includes a sheath tube 21, and a sheath hub 22 fixed to the proximal end of the sheath tube 21.

As shown in FIGS. 1 to 9, the sheath tube 21 is a tubular body, and is open at the distal end of the tubular body and the proximal end of the tubular body. The distal opening functions as a discharge port for the stent 10 at the time of indwelling the stent 10 at a lesion in a living body. When the stent 10 is discharged from the distal opening, the stent 10 automatically radially outwardly expands in response to removal of a stress load thereon, to be restored to its pre-compression shape. A distal portion of the sheath tube 21 constitutes a stent-containing part 21a that contains the stent 10. In addition, the sheath tube 21 has a side hole 23 provided on proximally of the stent-containing part 21a. The side hole 23 is for leading out a guide wire to the outside.

The outside diameter of the sheath tube 21 is preferably 0.5 to 4.0 mm, more preferably 0.8 to 2.0 mm. The inside diameter of the sheath tube 21 is preferably 0.2 to 1.8 mm. The length of the sheath tube 21 is preferably 300 to 2500 mm, more preferably 300 to 2000 mm.

The material forming the sheath tube 21 is selected taking into account the physical properties (flexibility, hardness, strength, slidability, anti-kinking property, stretching/contracting properties) required of a sheath tube. Preferred examples of the material include polyethylene, polypropylene, nylon, polyethylene terephthalate, fluoro-polymers such as PTFE, ETFE, etc. and, further, thermoplastic elastomers. The thermoplastic elastomers are appropriately selected from among those based on nylon (e.g., polyamide elastomer), those based on urethane (e.g., polyurethane elastomer), those based on polyester (e.g., polyethylene terephthalate elastomer), and those based on olefin (e.g., polyethylene elastomer, polypropylene elastomer).

Further, the outer surface of the sheath 2 is preferably treated to exhibit lubricity. Such a treatment may involve, for example, coating the outer surface of the sheath 2 with a hydrophilic polymer such as poly (2-hydroxyethyl methacrylate), polyhydroxyethyl acrylate, hydroxypropyl cellulose, methyl vinyl ether-maleic anhydride copolymer, polyethylene glycol, polyacrylamide, polyvinylpyrrolidone, and dimethylacrylamide-glycidyl methacrylate copolymer, or fixation of such a hydrophilic polymer to the outer surface. The inner surface of the sheath tube 21 may also be coated with the above-mentioned hydrophilic polymer or may have the hydrophilic polymer fixed thereto in order to achieve good slidability of the surface relative to the stent 10 and the shaft section 3.

Figure 8:
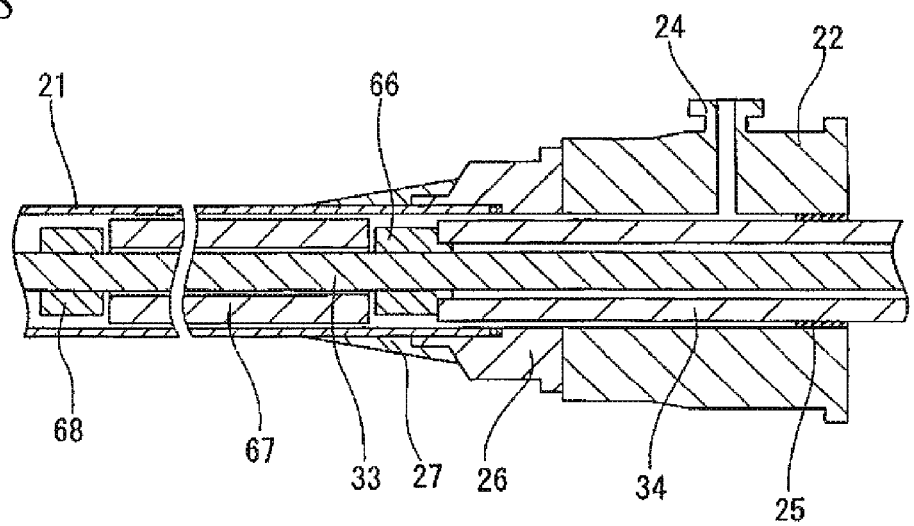
FIG. 8 is a cross-sectional view of the inner tube body of the stent delivery system shown in FIG. 1.

As shown in FIGS. 1 to 3 and 8, the sheath hub 22 is fixed to a proximal portion of the sheath tube 21. FIG. 8 illustrates that the sheath hub 22 is provided with a seal member 25 for holding the shaft section 3 in a slidable and liquid-tight manner. The seal member 25 is thus positioned between the inner surface of the sheath hub 22 and the outer surface of an intermediate portion of the shaft section 3. The sheath hub 22 has a side port 24.

The material constituting the sheath hub 22 is preferably a hard or semi-hard material. Examples of the hard or semi-hard material which can be used here include synthetic resins such as polycarbonate, polyolefins (e.g., polyethylene, polypropylene, ethylene-propylene copolymer), styrene resins [e.g., polystyrene, MS resin (methacrylate-styrene copolymer), MBS resin (methacrylate-butylene-styrene copolymer)], polyesters, etc. and metals such as stainless steel, aluminum, aluminum alloys, etc.

The materials constituting the seal member 25 and an elastic ring 69 which will be described later are preferably elastic materials. Examples of the elastic materials include rubbers such as synthetic rubbers, e.g., urethane rubber, silicone rubber, or butadiene rubber, and natural rubbers, e.g., latex rubber; and synthetic resin elastomers such as olefin elastomers (e.g., polyethylene elastomer, polypropylene elastomer), polyamide elastomers, styrene elastomers (e.g., styrene-butadiene-styrene copolymer, styrene-isoprene-styrene copolymer, styrene-ethylenebutylene-styrene copolymer), polyurethane, urethane elastomers, and fluoro-resin elastomers.

A distal portion of the sheath hub 22 is provided with reinforcement members 26, 27 extending distally beyond the distal end of the sheath hub.

As shown in FIGS. 1 to 6, the shaft section (inner tube body) 3 includes a shaft body 33, a distal-side tube 31 at the distal end of the shaft body 33 and protruding distally beyond the distal end of the sheath 2, and a shaft hub 30 fixed to a proximal portion of the shaft body 33.

In this embodiment, the shaft section 3 is provided with a proximal-side opening of the guide wire lumen that opens at a side portion on the proximal side relative to the stent-containing part of the sheath 2, and the sheath 2 has the side hole 23 provided on the proximal side relative to the stent-containing part. A guide wire can be inserted and passed through the side hole 23 in the sheath 2 and the proximal-side opening in the shaft section 3.

Figure 5:
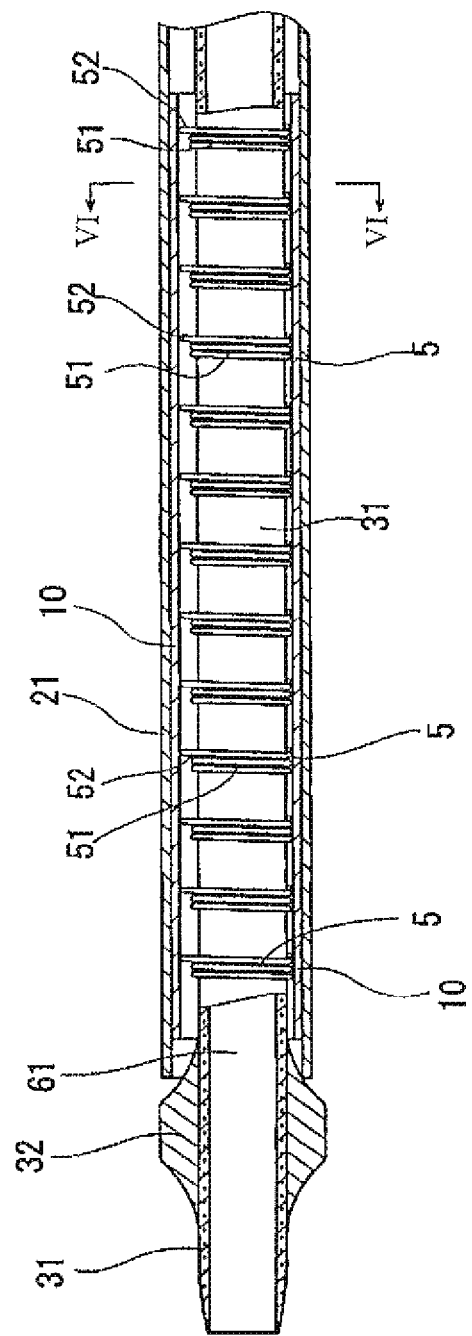
FIG. 5 is a partial cross-sectional view in the vicinity of the distal portion of the stent delivery system shown in FIG. 1.
Figure 7:
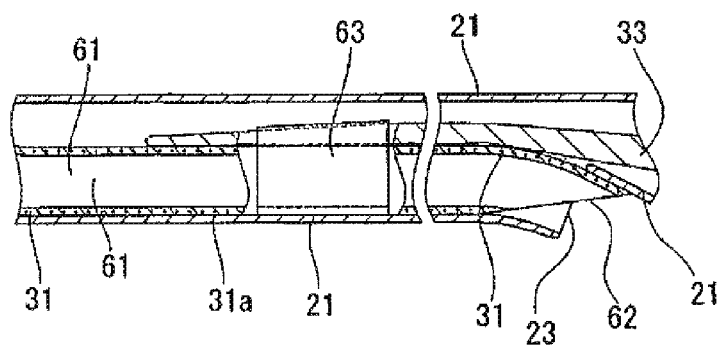
FIG. 7 is a cross-sectional view of the internal structure in the vicinity of an intermediate portion of the stent delivery system shown in FIG. 1.

As shown in FIG. 5, the distal-side tube 31 protrudes distally beyond the distal end of the sheath 2. In addition, the distal-side tube 31 is provided with a stopper 32 for inhibiting the sheath 2 from moving in the distal direction beyond the stopper 32. As shown in FIG. 7, a proximal portion of the distal-side tube 31 is curved, enters into the side hole 23 of the sheath tube 21, and is releasably engaged with the side hole 23. The outside diameter of the distal-side tube 31 is preferably 0.2 to 1.8 mm. As shown in FIG. 5, a distal portion of the distal-side stopper 32 preferably decreases in outer diameter toward the distal direction. The outside diameter at a largest diameter part of the stopper 32 is preferably 0.5 to 4.0 mm. In addition, a proximal portion of the stopper 32 also preferably decreases in outer diameter toward the proximal direction, as shown in FIG. 5. The distal-side tube 31 has the guide wire lumen 61 extending from the distal end of the distal-side tube 31 to the proximal end of the distal-side tube 31, and the proximal opening 62 of the guide wire lumen 61 is positioned proximally of the distal-most end of the distal-side tube 31. The proximal opening 62 of the guide wire lumen 61 is preferably spaced proximally relative to the distal-most end of the distal-side tube 31 by 10 to 400 mm, particularly 50 to 350 mm. The proximal opening 62 is preferably also spaced proximally relative to the rear end (proximal-most end) of the stent 10 (in other words, the rear end of the stent-containing part) by about 50 to 250 mm.

The outer surface of the inner tube body 3 is provided with elastic members 5 which press the stent 10 in the direction toward the stent-containing tube body 2. The stent 10 is clamped between the elastic members 5 and the stent-containing tube body 2 and is adapted to be slidable relative to the stent-containing tube body 2. In addition, the stent 10 is not substantially slidable relative to the elastic members 5.

Figure 6:
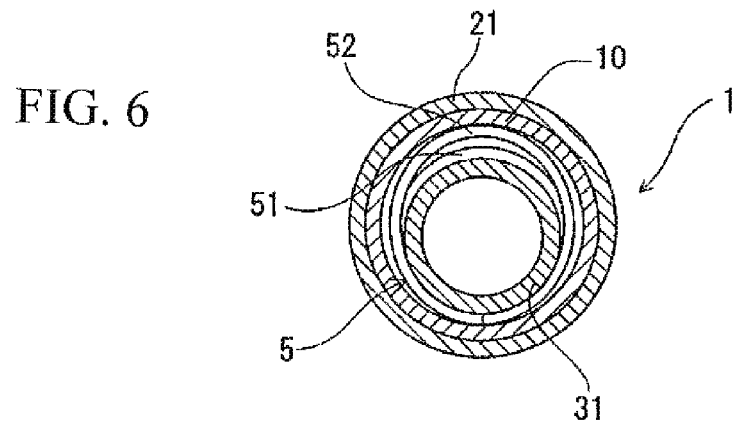
FIG. 6 is an enlarged cross-sectional view taken along the section line VI-VI of FIG. 5.

In the stent delivery system 1 according to this embodiment, the elastic members 5 are fixed to the outer surface of the inner tube body 3 (specifically, the distal-side tube 31). As shown in FIGS. 5 and 6, the elastic members 5 are wire coils each of which has a fixation section 51 for fixation to the distal-side tube 31 and an elastic section 52 for pressing the stent 10. The fixation section 51 is formed by winding a wire, constituting the wire coil, around the distal-side tube 31. As shown in FIGS. 5 and 6, the elastic section 52 is configured by a structure in which the wire forming the fixation section 51 is separated from the distal-side tube 31 (spaced from the outer surface of the distal-side tube 31) and spread in the radial direction.

The elastic section 52 has a size and a spring elasticity which make it possible to press the stent 10 contained in the sheath 2. In addition, in this embodiment, as shown in FIG. 5, at least the elastic section 52 of the elastic member 5 composed of the wire coil is preferably a little inclined relative to a plane orthogonal to the axial direction of the stent delivery system 1.

The inclined configuration of elastic section 52 of the elastic member 5 composed of the wire coil helps ensure better pressing of the stent 10. The elastic section 52 of the elastic member 5 composed of the wire coil is preferably so adapted that it is deformed so as to fall to the proximal side, through transmission of a stress thereto, upon pulling of the stent-containing tube body (sheath) 2 proximally relative to the inner tube body 3 and that it is deformed so as to fall to the distal side, through transmission of a stress thereto, upon pushing of the stent-containing tube body (sheath) 2 distally relative to the inner tube body 3. That is, the elastic section 52 tends to incline when the sheath 2 is pulled or pushed. In this embodiment, as shown in FIGS. 5 and 6, the elastic member 5 is adapted to press at least a part of the inner circumference of the stent 10.

The stent delivery system 1 according to this embodiment disclosed by way of example includes a plurality of the elastic members 5. Particularly, in the stent delivery system 1 shown in FIG. 5, the plurality of elastic members 5 are provided in the area ranging from the distal portion of the stent to the proximal portion of the stent 10. The elastic members 5 are also arranged at substantially regular intervals. Further, in the stent delivery system 1 shown in FIG. 5, each of the elastic members 5 is adapted to contact and press (apply a force to) at least a part of the inner circumference or inner surface of the stent 10, and the stent parts pressed by each of the elastic members 5 are arranged substantially rectilinearly along the axial direction of the stent.

Figure 10:
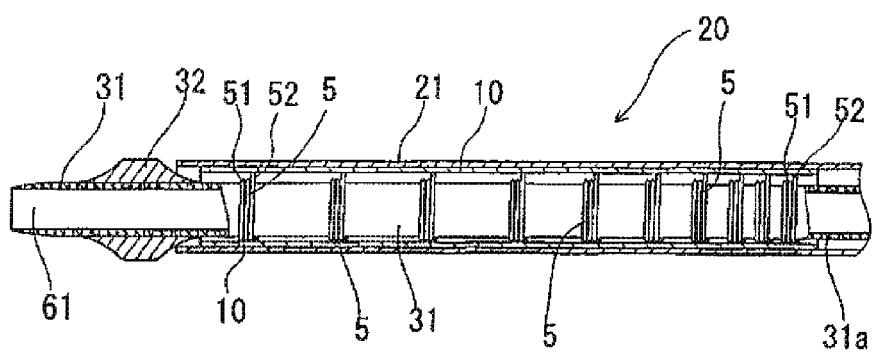
FIG. 10 is a cross-sectional view in the vicinity of a distal portion of a stent delivery system according to another embodiment disclosed by way of example here.

The elastic members are preferably provided as a plurality of elastic members and may be present in a relatively larger number on the proximal side of the stent (closer to the proximal-most end of the stent than the distal-most end of the stent). For example, as in a stent delivery system 20 according to an embodiment shown in FIG. 10, a plurality of the elastic members may be arranged so that the interval between axially adjacent elastic members decreases toward the proximal direction of the stent. This configuration helps enhance a gripping force for the stent on the proximal side.

Figure 11:
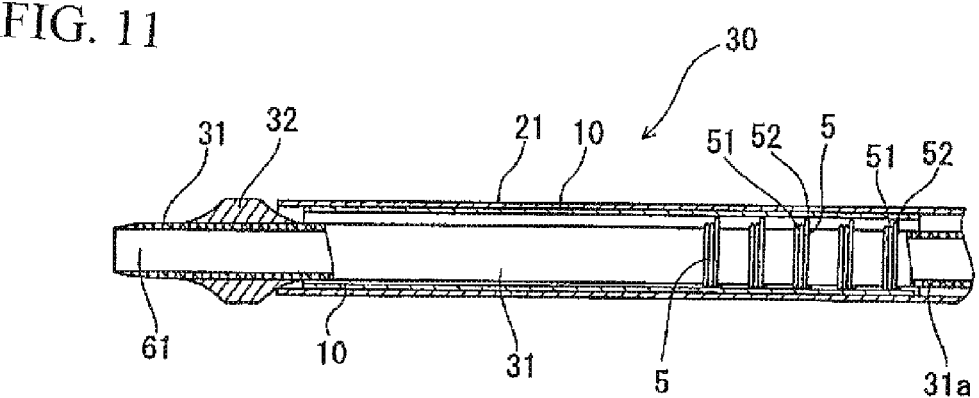
FIG. 11 is a cross-sectional view in the vicinity of a distal portion of a stent delivery system according to a further embodiment disclosed by way of example here.

It is also possible that only one of the elastic members 5 is provided within a proximal portion of the stent 10. Furthermore, the stent delivery system 30 can be in the configuration shown in FIG. 11 in which a plurality of the elastic members 5 are provided in the area ranging from the central portion to the proximal portion of the stent, whereas no elastic member is disposed in the area ranging from the central portion to the distal portion of the stent.

Figure 12:
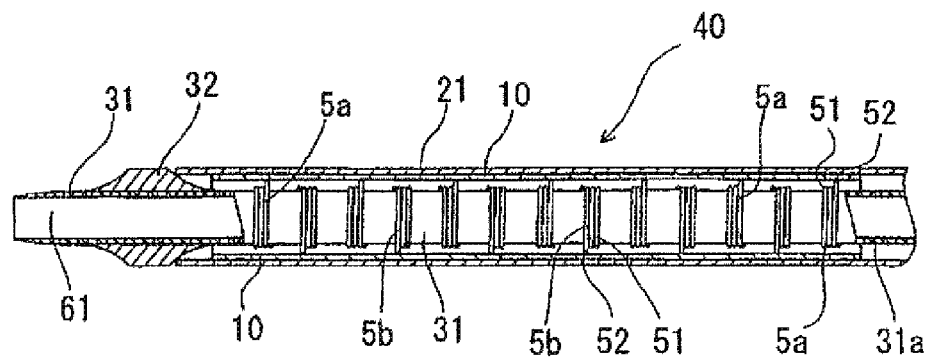
FIG. 12 is a cross-sectional view in the vicinity of a distal portion of a stent delivery system according to yet another embodiment disclosed by way of example here.
Figure 13:
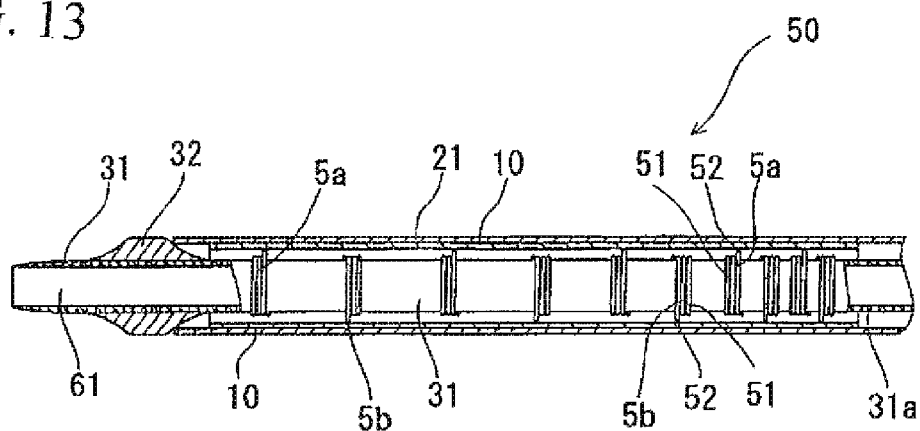
FIG. 13 is a cross-sectional view in the vicinity of a distal portion of a stent delivery system according to a yet further embodiment disclosed by way of example here.

FIG. 12 illustrates another possibility in which the stent delivery system 40 is configured so that a plurality of elastic members 5a, 5b are provided, each of the elastic members 5a, 5b is adapted to press at least a part of the inner surface or inner circumference of the stent 10, and the stent parts pressed by the axially adjacent elastic members differ from each other as viewed along the axial direction of the stent. In the stent delivery system 40 according to this embodiment, two kinds of elastic members 5a, 5b are provided such that the parts of the stent 10 which are pressed respectively by the two kinds of elastic members 5a, 5b are at an angular interval of about 180 degrees around the center axis of the stent. That is, parts of the stent 10 which are pressed respectively by the two kinds of elastic members 5a, 5b are circumferentially spaced apart by about 180 degrees. The projecting directions of the elastic sections 52 of the elastic members 5a and 5b are thus at an angular interval of about 180 degrees around center axis of the stent. The stent delivery system 40 according to this embodiment is also configured so that the elastic members 5a and the elastic members 5b are arranged alternately. Therefore, those parts of the stent which are pressed by the elastic members 5a, 5b are arranged in a zigzag manner along the axial direction of the stent. This helps ensure balanced gripping of the stent as a whole. While the projected elastic sections of the adjacent elastic members are at an angular (circumferential) shift of about 180 degrees in the above-mentioned embodiment, the angular shift between the projected elastic sections of the adjacent elastic members may be, for example, 45 to 120 degrees so that the projected elastic sections are arranged spirally. In addition, in this type of sent delivery system, also, the elastic members may be present in a larger number on the proximal side of the stent, as shown in FIG. 13. In a stent delivery system 50 according to an embodiment shown in FIG. 13, the elastic members 5a, 5b are so arranged that the interval between the elastic member 5a and the elastic member 5b decreases toward the proximal direction of the stent.

In the case where a plurality of the elastic members are provided, the intervals of the elastic members are preferably 0.1 to 10 mm, particularly preferably 1 to 5 mm.

Figure 14:
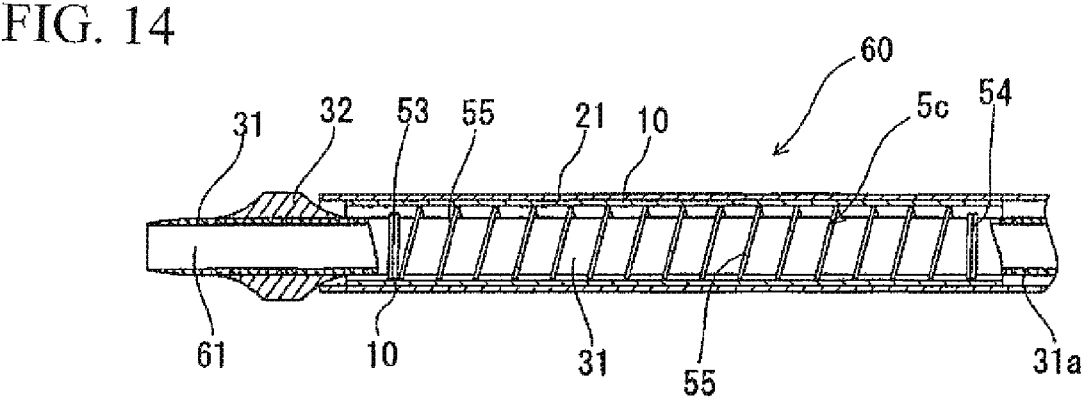
FIG. 14 is a cross-sectional view in the vicinity of a distal portion of a stent delivery system according to still another embodiment disclosed by way of example here.

In a stent delivery system 60 according to an embodiment shown in FIG. 14, an elastic member 5c may be a wire coil having a starting end side fixation section 53 and a terminal end side fixation section 54, which are for fixation to the inner tube body 31, and a spirally shaped stent-pressing elastic section 55 between the starting end side fixation section 53 and the terminal end side fixation section 54 and extending over a predetermined length along the axial direction of the stent 10. This elastic member 5c is formed of a single wire, with one end portion wound around the inner tube body 31 to form the starting end side fixation section 53, and the other end portion wound around the inner tube body 31 to form the terminal end side fixation section 54. The elastic member 5c may also be configured so that the terminal end side is unfixed to the inner tube body, thereby forming a free end. The spirally shaped stent-pressing elastic section 55 projects in a direction of a specified part of the inner surface or inner circumference of the stent 10, thereby pressing at least a part of the inner surface or inner circumference of the stent. Consequently, those stent parts which are pressed by the spirally shaped stent-pressing elastic section 55 are arranged substantially rectilinearly along the axial direction of the stent.

Figure 15:
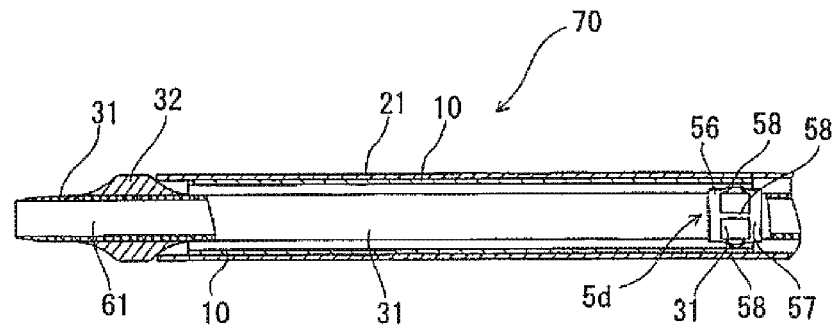
FIG. 15 is an illustration of an operation aspect of the stent delivery system.

In addition, FIG. 15 illustrates a stent delivery system 70 according to another embodiment. Here, an elastic member 5d has a starting end side fixation section 56 and a terminal end side fixation section 57 for fixation to the inner tube body 31, and leaf spring-configured stent-pressing elastic sections 58 between the starting end side fixation section 56 and the terminal end side fixation section 57, extending over a predetermined length along the axial direction of the stent 10 and projecting at central portions of the elastic sections. This elastic member 5d is not a wire coil as mentioned above. The elastic member 5d may be kept unfixed to the inner tube body on the terminal end side, thereby forming a free end. This elastic member 5d has a plurality of the stent-pressing elastic sections 58 which press a plurality of parts (spaced-apart parts) of the inner peripheral surface or the inner circumference of the stent 10 at which the elastic member 5d is disposed.

The elastic member 5d is a tubular body provided with a plurality of cutouts in a central portion thereof. The starting end side fixation section 56 and the terminal end side fixation section 57 are fixed to the inner tube body 31 by caulking. In addition, the elastic member 5d has the leaf spring-configured stent-pressing elastic sections 58 formed by deforming a plurality of (specifically, four) central portions thereof so as to project outward. The stent delivery system 70 shown in FIG. 15 is illustrated as including only one elastic member 5d disposed at a proximal portion of the stent 10. But it is also possible to configure the stent delivery system 70 to include a plurality of such elastic members 5d, like in the stent delivery systems 1, 20, 30 according to other embodiments discussed above.

The material for the wire coil forming the elastic member can be a metallic wire such as stainless steel wire (preferably, high tensile stainless steel wire for spring), piano wire (preferably, nickel-plated or chromium-plated piano wire), etc. or a linear material made of a comparatively highly rigid polymeric material such as polyamides, polyimides, ultra-high-molecular weight polyethylene, polypropylene, fluoro-resin, etc.

In addition, the elastic member 5 may possess radiopacity characteristics. This helps ensure that the position in the vicinity of a proximal portion of the stent can be determined under radioscopy, which helps facilitate an easier procedure. The radiopacity can be imparted by forming the elastic member 5 from a radiopaque material or by coating the elastic member 5 with a radiopaque material. Preferable examples of the radiopaque material include gold, platinum, platinum-iridium alloy, silver, stainless steel, and their alloys.

In the stent delivery system 1 disclosed here, the inner tube body 3 (specifically, the distal-side tube 31) has the opening 62 communicating with the guide wire lumen on the proximal side relative to the stent-containing part of the stent-containing tube body 2.

In addition, the distal-side tube 31 is preferably provided with a reinforcement layer 31a at least at a part on the proximal side relative to a rear end portion of the stent. In the system according to this embodiment, the reinforcement layer 31a is provided over the whole of the distal-side tube 31. The reinforcement layer 31a may be not provided at a distal-most portion of the distal-side tube 31. The reinforcement layer 31a is preferably a meshed reinforcement layer. The meshed reinforcement layer is preferably formed of braids. The braids can be formed, for example, of wires of a metal such as stainless steel, elastic metals, superelastic alloys, and shape memory alloys of a wire diameter of 0.01 to 0.2 mm, preferably 0.03 to 0.1 mm. Or, alternatively, the braids may be formed of synthetic fibers such as polyamide fibers, polyester fibers, and polypropylene fibers.

The shaft body 33 includes a distal portion fixed to a proximal portion of the distal-side tube 31, a main body portion extending over a predetermined length in the proximal direction from the distal portion, and a proximal portion protruding beyond the shaft hub 30. In this embodiment, the distal portion of the shaft body 33 fixed to the distal-side tube 31 is a smaller diameter section, and the main body portion and the proximal portion are greater in outer diameter than the smaller diameter section of the shaft body 33. In this embodiment, the distal portion of the shaft body 33 is fixed to a side surface of the distal-side tube 31 by a heat-shrinkable tube 63.

The length of the shaft section 3 is preferably 400 to 2500 mm, particularly preferably 400 to 2200 mm. In addition, the outside diameter of the main body portion of the shaft body 33 is preferably 1.0 to 2.5 mm, particularly preferably 1.0 to 2.0 mm. The length of the distal-side tube 31 is preferably 10 to 400 mm, particularly preferably 50 to 350 mm; and its outside diameter is preferably 0.2 to 2.0 mm. The inside diameter of the lumen 61 is preferably 0.2 to 2.0 mm, particularly preferably 0.3 to 1.0 mm.

The shaft body 33 may be solid, or may be tubular. In addition, it may be a coil shaft. The material forming the shaft section 3 is preferably a material which has hardness and a certain degree of flexibility. Preferable examples of the shaft section 33 which can be preferably used here include wires or pipes of a metal such as stainless steel, superelastic metals, etc. or bar-like bodies or tubular bodies of polyethylene, polypropylene, nylon, polyethylene terephthalate, fluoropolymers such as ETFE, PEEK (polyether ether ketone), polyimide, etc. An outer surface of the shaft section 3 may be coated with a biocompatible material, particularly an antithrombogenic material. Examples of the antithrombogenic material which can be preferably used here include polyhydroxyethyl methacrylate, and hydroxyethyl methacrylate-styrene copolymers (e.g., HEMA-St-HEMA block copolymer).

Further, the outer surface of that portion of the shaft section 3 which may protrude beyond the sheath 2 preferably has lubricity. In view of this, the outer surface of the portion which may protrude beyond the sheath 2 may be coated with a hydrophilic polymer such as poly (2-hydroxyethyl methacrylate), polyhydroxyethyl acrylate, hydroxypropyl cellulose, methyl vinyl ether-maleic anhydride copolymer, polyethylene glycol, polyacrylamide, polyvinylpyrrolidone, dimethylacrylamide-glycidyl methacrylate copolymer, etc. or may have the hydrophilic polymer fixed thereto. Or, alternatively, the whole of the outer surface of the shaft section 3 may be coated with the hydrophilic polymer or the hydrophilic polymer may be fixed to the whole of the outer surface of the shaft section 3. Furthermore, the inner surface of the shaft section 3 may also be coated with the hydrophilic polymer or the hydrophilic polymer may be fixed to the inner surface of the shaft section 3 for the purpose of enhancing slidability of the inner surface of the shaft section 3 relative to the guide wire.

Figure 2:
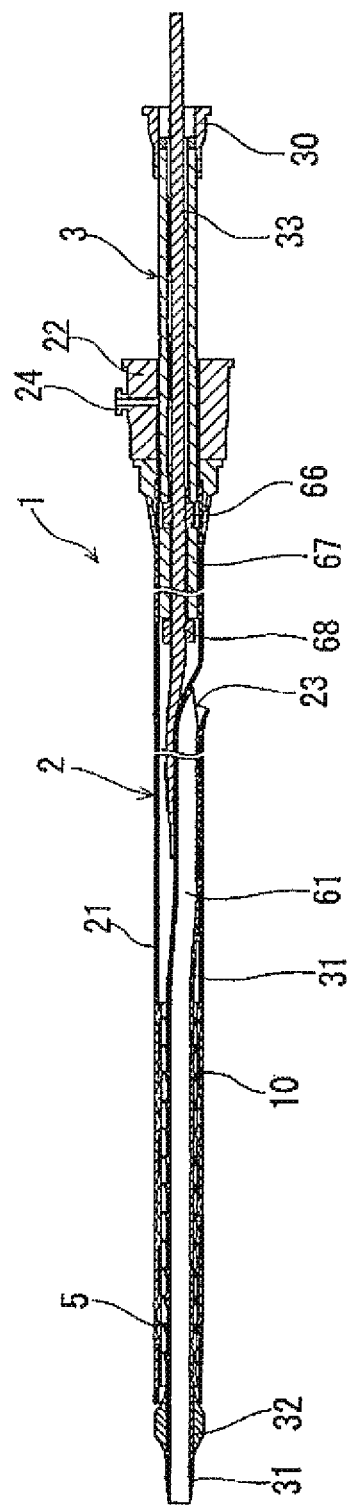
FIG. 2 is a longitudinal cross-sectional view of the stent delivery system shown in FIG. 1.
Figure 3:
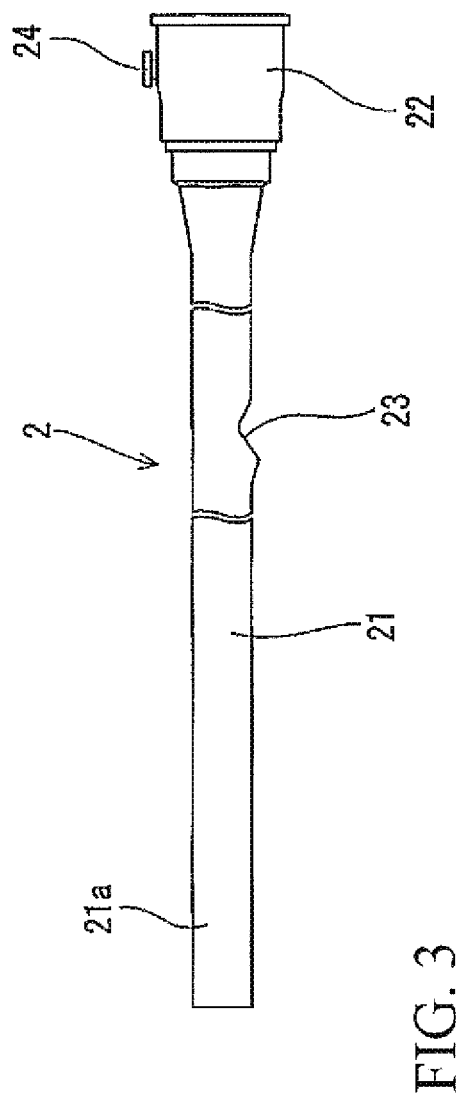
FIG. 3 is a side view of the stent-containing tube body (sheath) of the stent delivery system shown in FIG. 1.
Figure 4:
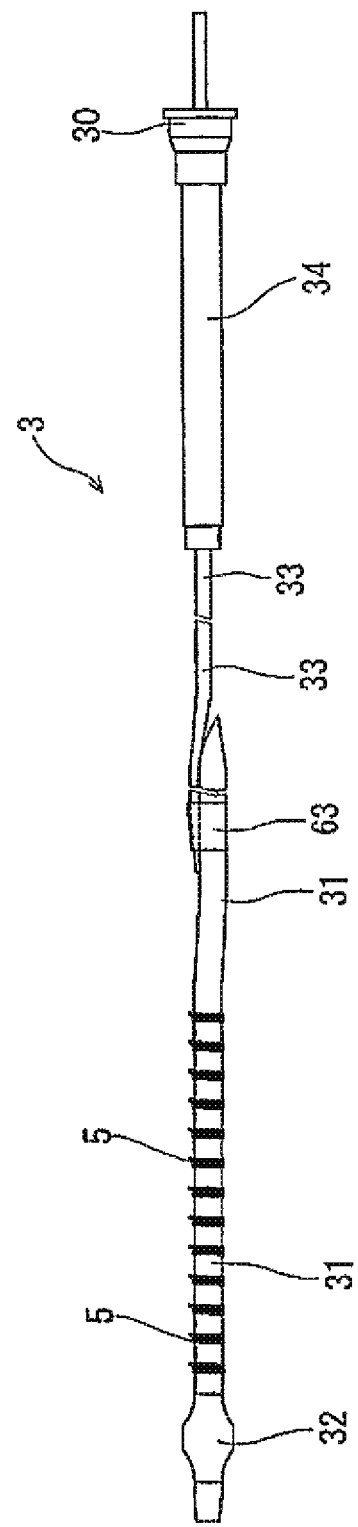
FIG. 4 is a side view of the inner tube body of the stent delivery system shown in FIG. 1.
Figure 9:
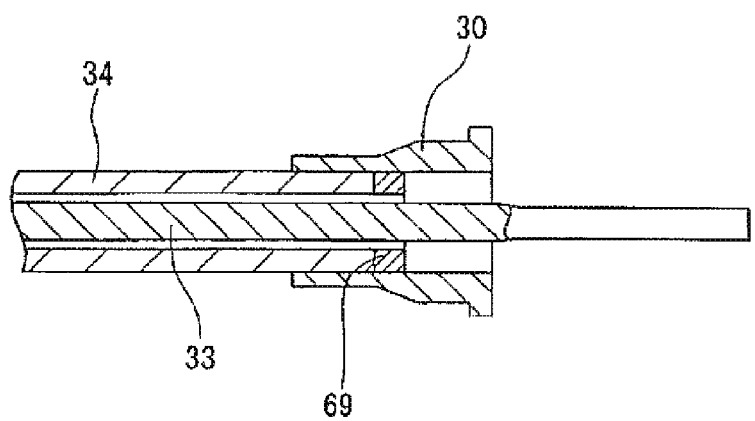
FIG. 9 is a cross-sectional view in the vicinity of a proximal portion of the stent delivery system shown in FIG. 1.

The shaft body 33 passes through (penetrates) the sheath 2 and protrudes proximally beyond the proximal opening of the sheath 2. As shown in FIGS. 1, 2 and 9, the shaft hub 30 is firmly attached to the shaft body in the vicinity of a proximal portion of the shaft body 33. In this embodiment, as shown in FIG. 8, a fixation ring 66 is fixed to the shaft body 33. A proximal-side tube 34 extending distally from the hub 30 is fixed to the shaft hub 30. In addition, a distal end portion of the proximal-side tube 34 is fixed to the fixation ring (first fixation ring) 66 as shown in FIG. 8. An elastic ring 69, shown in FIG. 9, is fixed at the proximal end of the proximal-side tube 34 and is positioned inside the shaft hub 30. A second fixation ring 68, shown in FIG. 2, is positioned on the distal side of the first fixation ring 66 and is spaced from the first fixation ring 66 by a predetermined distance in this embodiment. In addition, an intermediate tube 67 is disposed between the first fixation ring 66 and the second fixation ring 68. The intermediate tube 67 is fixed neither to the shaft body 33 nor to the sheath tube 21, and is configured to be able to make contact with the first fixation ring 66 and the second fixation ring 68. The intermediate tube helps ensure good sliding of the sheath. The material forming the intermediate tube 67 is preferably a material having a low-friction outer surface. Specific examples of the intermediate tube include tubes formed from polyethylene, polypropylene, nylon, polyethylene terephthalate, or fluoro-polymer such as PTFE and ETFE.

The stent 10 used in the stent delivery system is a so-called self-expandable stent which can be restored to its pre-compression shape by automatically expanding outwardly when indwelled in a living body. Further, the stent 10 has a distal portion and a proximal portion which extend respectively to the distal side and the proximal side of the sheath 2. Furthermore, the stent 10 is configured so that, except for the proximal portion, there are no bent free ends that protrude toward the proximal end. That is, other than the proximal portion, the stent does not include portions, extending toward the proximal end, which are both bent and unconnected to another portion (another strut) of the stent. In addition, by moving the sheath 2 distally after exposing a distal portion of the stent 10 from the sheath 2, the exposed distal portion of the stent 10 can be re-contained into the sheath 2.

The stent to be used may have a structure in which vertices of proximal-side bent portions or portions near the vertices of proximal-side bent portions are connected to other linear elements so that the stent does not have any free end. In addition, the stent to be used may be one of those shown in FIGS. 18 and 19.

The stent 10 includes wavy struts 13, 14 which extend in the axial direction from one end to the other end of the stent. The plurality of wavy struts 13, 14 are arranged in the circumferential direction of the stent. The stent 10 also includes one or a plurality of connecting struts 15 which interconnect the respective adjacent wavy struts and extend in the axial direction over a predetermined distance. Further, each of end portions of the wavy struts 13, 14 is connected to an end portion of the adjacent wavy strut.

Figure 18:
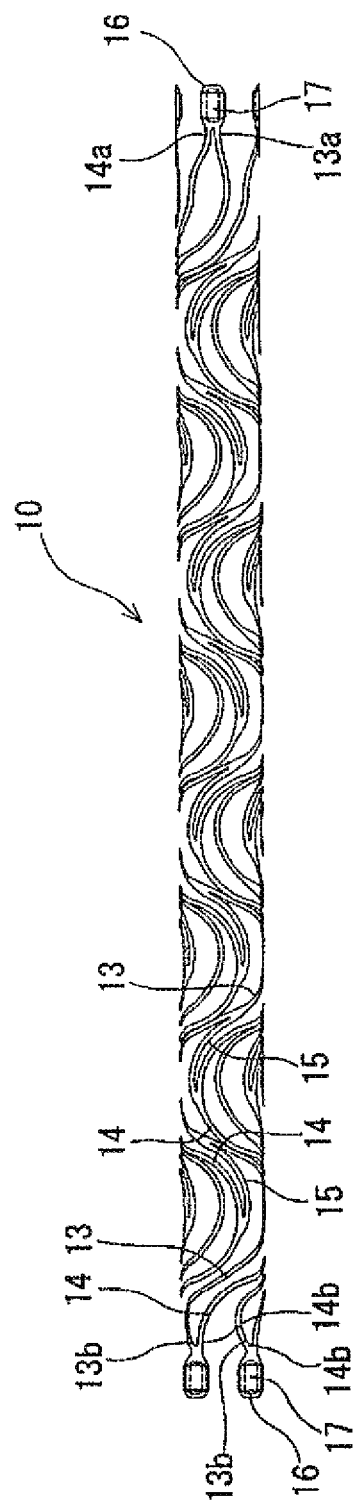
FIG. 18 is a side view of an example of a stent for placement in a living body to be used in the stent delivery system.
Figure 19:
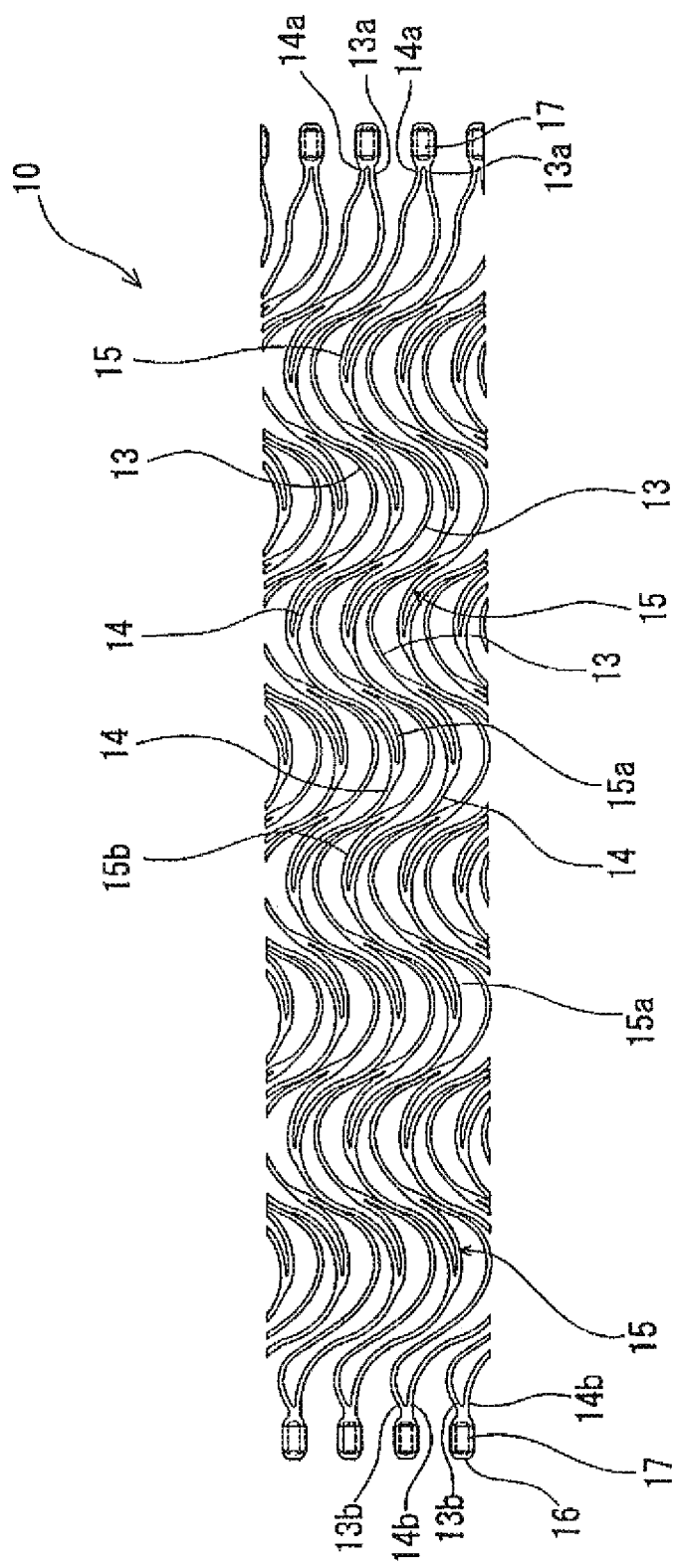
FIG. 19 is a development view of the stent shown in FIG. 18.

More specifically, the stent 10 shown in FIGS. 18 and 19 includes: a plurality of first wavy struts 13 which extend in the axial direction from one end to the other end of the stent and are arranged in the circumferential direction of the stent; a plurality of second wavy struts 14 which are each located between the first wavy struts 13, extend in the axial direction from one end side to the other end side of the stent and are arranged in the circumferential direction of the stent; and one or a plurality of connecting struts 15 which interconnect the first wavy strut 13 and the second wavy strut 14 adjacent to each other and extend in the axial direction over a predetermined distance. The vertices of the second wavy strut 14 deviate by a predetermined distance in the axial direction of the stent relative to the vertices of the first wavy strut 13 which is adjacent thereto in the circumferential direction of the stent 10 and is curved in the same direction. In addition, end portions 13a, 13b of the first wavy strut 13 are connected to end portions 14a, 14b of the circumferentially adjacent second wavy strut.

The stent 10 in this example is a so-called self-expandable stent which possesses a substantially hollow cylindrical shape, is compressed toward its center axis at the time of insertion into a living body, and is automatically restored to its pre-compression shape by expanding outward when indwelled in the living body.

Describing aspects of the stent in more detail, the first wavy struts 13 extend along the axial direction substantially parallel to the center axis of the stent, and are arranged, plural in number, in the circumferential direction of the stent. The number of first wavy struts 13 is preferably at least 3, and particularly preferably about 3 to 8. Further, the plural first wavy struts 13 are preferably arranged at substantially regular angular intervals around the center axis of the stent.

The second wavy struts 14 also extend along the axial direction substantially parallel to the center axis of the stent and are arranged plural in number in the circumferential direction of the stent. Each of the second wavy struts 14 is positioned between two circumferentially adjacent first wavy struts 13. The number of second wavy struts 14 is preferably at least 3, and particularly preferably about 3 to 8. Further, the plural second wavy struts 14 are preferably arranged at substantially regular angular intervals around the center axis of the stent. In addition, the number of second wavy struts 14 is preferably the same as the number of first wavy struts 13.

The stent 10 has one or a plurality of connecting struts 15 which interconnect the first wavy strut 13 and the second wavy strut 14 adjacent to each other and extend in the axial direction over a predetermined distance. Particularly, in the stent 10 in this example, the connecting strut 15 has one end in the vicinity of an inflection point of a wavy strut of one side, has the other end in a region ranging from the vicinity of a vertex to a portion a little beyond the vertex of the adjacent wavy strut of the other side, extends in the axial direction, and is curved in the same direction as the vertex of the wavy strut of the other side. Specifically, as shown in FIG. 19, the connecting strut 15 is composed of a first connecting strut 15a so curved as to have a vertex protruding to one side in the circumferential direction of the stent 10, and a second connecting strut 15b so curved as to have a vertex protruding to the other side in the circumferential direction of the stent 10. In addition, the connecting strut 15 is curved in an arcuate shape and has substantially the same radius as that of the arc of the curved portion of the first wavy strut 13 or second wavy strut 14 adjacent thereto in the circumferential direction of the stent 10.

The stent 10 in this example also has coupling parts 16 by which every one of the end portions of all the first wavy struts is coupled to an end portion of one of the circumferentially adjacent second wavy struts. Specifically, an end portion 13a at one end of the first wavy strut in the stent 10 is coupled with an end portion 14a of one of the circumferentially adjacent second wavy struts 14 (specifically, the second wavy strut 14 adjacent to and on the circumferentially other side of the first wavy strut) by the coupling part 16. In addition, an end portion 13b at the other end of the first wavy strut is coupled with an end portion 14b of one of the circumferentially adjacent second wavy struts 14 (specifically, the second wavy strut 14 adjacent to and on the circumferentially one side of the first wavy strut) by the coupling part 16. In other words, in the coupling parts 16 at one end and the coupling parts 16 at the other end, the combinations of the first wavy strut 13 and the second wavy strut 14 coupled together are different (shifted by one each).

A radiopaque marker 17 is attached to the coupling part 16. In this example, the coupling part 16 has two frame portions extending in parallel and at a predetermined interval in the end portion direction, and the radiopaque marker 17 is adapted to cover substantially the whole or a part of the two frame portions. In addition, the radiopaque marker 17 has a thin rectangular parallelepiped shape, contains the two frame portions therein, and is recessed in a central portion thereof, whereby it is fixed to the two frame portions. The material forming the radiopaque marker can be, for example, one element (elemental metal) or at least two elements (alloy) selected from the group consisting of iridium, platinum, gold, rhenium, tungsten, palladium, rhodium, tantalum, silver, ruthenium, and hafnium.

The material constituting the stent 10 is preferably a superelastic metal. As the superelastic metal, a superelastic alloy is preferably used. The superelastic alloy herein means an alloy which is generally called a shape memory alloy and which exhibits superelasticity at least at a living body temperature (around 37° C.). Particularly, such superelastic metals as Ti—Ni alloys containing 49 to 53 atomic % of Ni, Cu—Zn alloys containing 38.5 to 41.5 wt. % of Zn, Cu—Zn—X alloys (X=Be, Si, Sn, Al, Ga) containing 1 to 10 wt. % of X, and Ni—Al alloys containing 36 to 38 atomic % of Al are used suitably. Especially preferred are the Ti—Ni alloys. Besides, the mechanical properties of superelastic alloys can be changed, as required, by a method in which part of the Ti—Ni alloys is replaced by 0.01 to 10.0% of X to form Ti—Ni—X alloys (X=Co, Fe, Mn, Cr, V, Al, Nb, W, B, etc.), a method in which part of the Ti—Ni alloys is replaced by 0.01 to 30.0% of atoms to form Ti—Ni—X alloys (X=Cu, Pb, Zr), or a method in which the conditions of cold working ratio and/or final heat treatment are selected. In addition, while using the above-mentioned Ti—Ni—X alloy, the cold working ratio and/or final heat treatment conditions may be selected, whereby the mechanical properties of the alloy can be changed, as required. Of the superelastic alloy to be used, the buckling strength (the yield stress under load) is 5 to 200 kg/mm$^2$ (22° C.), preferably 8 to 150 kg/mm$^2$, and the restoring stress (the yield stress when unloaded) is 3 to 180 kg/mm$^2$ (22° C.), preferably 5 to 130 kg/mm$^2$. The term superelasticity here means a property of a metal such that even upon deformation (bending, extension, compression) of the metal into a region where ordinary metals undergo plastic deformation at use temperature, the deformed metal is restored substantially into its pre-compression shape after release of the deformation, without needing heating.

In addition, the diameter of the stent when compressed is preferably 0.5 to 1.8 mm, particularly preferably 0.6 to 1.4 mm. The length of the stent when not compressed is preferably 5 to 200 mm, particularly preferably 8.0 to 100.0 mm. In addition, the diameter of the stent when not compressed is preferably 1.5 to 6.0 mm, particularly preferably 2.0 to 5.0 mm. Further, the material thickness of the stent is preferably 0.05 to 0.40 mm, particularly preferably 0.05 to 0.15 mm. The width of the wavy struts is preferably 0.01 to 1.00 mm, particularly preferably 0.05 to 0.2 mm. Surfaces of the wavy struts are preferably in the state of having been processed to be smooth; in this case, smoothening is preferably carried out by electropolishing. The strength of the stent in the radial direction is preferably 0.1 to 30.0 N/cm, particularly preferably 0.5 to 5.0 N/cm.

Figure 16:
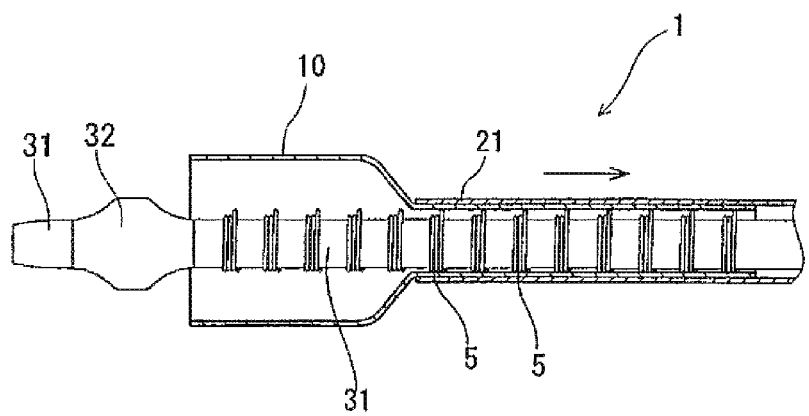
FIG. 16 is an illustration of another operation aspect of the stent delivery system.
Figure 17:
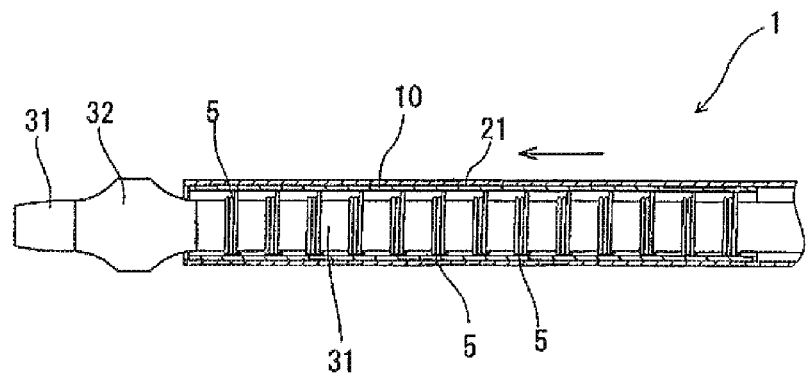
FIG. 17 is an illustration of a further operational aspect of the stent delivery system.

Now, operation of the stent delivery system disclosed here is described below with reference to FIGS. 16 and 17.

The stent delivery system 1 is inserted into a blood vessel to be therapeutically treated, and the stent delivery system is moved to position the stent at an indwelling position. In this state, the stent 10 as a whole is contained in the sheath 2. Then, the sheath 2 is moved proximally relative to the shaft section 3, whereby the stent 10 is exposed from the distal opening of the sheath 2, as shown in FIG. 16. The stent 10 exposed from the sheath 2 tends to be restored to its pre-compression form through expansion by its self-expanding force. In this stent delivery system 1, however, the stent 10 at the non-exposed portion is clamped between the elastic member 5 and the sheath 2; therefore, in the case where the position of the stent 10 should be readjusted, the stent 10 can be re-contained into the sheath by moving the sheath 2 distally relative to the shaft section 3, as shown in FIG. 17. Then, after an adjustment for bringing the stent portion to an appropriate position, the sheath 2 is again moved proximally relative to the shaft section 3, whereby the stent 10 is exposed from the distal opening of the sheath 2, as shown in FIG. 16. Then, the sheath 2 is moved proximally until the proximal end of the stent is exposed, whereby the stent is discharged completely from the sheath, to be released from the shaft section 3.

The stent delivery system is thus configured to clamp, grip or hold the stent to inhibit or prevent the stent from jumping out of the stent-containing tube body in an unguarded manner as might otherwise be the case in the absence of the stent being held, gripped or clamped. When the stent has been partially exposed, but still remains partially gripped, held or clamped, it is possible to re-contain the exposed part of the stent into the stent-containing tube body. This allows the position of placement of the stent to be changed or corrected, thus allowing the stent to be reliably placed at a desired target site.

The detailed description above describes a stent delivery system according to several embodiments disclosed by way of example. The invention here is not limited, however, to the precise embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent delivery system comprising:
   an inner tube body having a guide wire lumen configured to receive a guide wire to guide movement of the stent delivery system;
   a stent-containing tube body surrounding a distal portion of the inner tube body so that a space exists between an outer surface of the inner tube body and an inner surface of the stent-containing tube body;
   a hollow longitudinally extending stent positioned in the space between the outer surface of the inner tube body and the inner surface of the stent-containing tube body so that the inner tube body passes through the stent, the stent being compressed while positioned in the space and being automatically expandable outwardly when exposed outside the stent-containing tube body, the stent possessing an inner surface, a proximal-most end and a distal-most end;
   an elastic member positioned in the space between the outer surface of the inner tube body and the inner surface of the stent-containing tube body, the elastic member being a wire coil comprised of a plurality of windings, at least one of the windings being a fixation section contacting the outer surface of the inner tube body to fix the elastic member to the inner tube body, at least an other of the windings being an elastic section contacting an inner surface of the stent only at a portion of the longitudinal extent of the stent so that the stent is clamped between the elastic member and the stent-containing tube body, the portion being located closer to the proximal-most end of the stent than the distal-most end of the stent, at least a part of the elastic section contacting the inner surface of the stent also being radially outwardly spaced from the outer surface of the inner tube body; and
   the stent-containing tube body being slidable proximally relative to the stent to expose the stent outside the stent-containing tube body and permit the stent to expand outwardly.

2. The stent delivery system according to claim 1, further comprising a plurality of the elastic members positioned in the space between the outer surface of the inner tube body and the inner surface of the stent-containing tube body, the plurality of elastic members being spaced apart from one another and contacting the inner surface of the stent at a plurality of spaced apart locations so that the stent is clamped between the elastic members and the stent-containing tube body, and wherein portions of the inner surface of the stent between the spaced apart locations are not contacted by any elastic members.

3. The stent delivery system according to claim 2, wherein the plurality of the elastic members include a plurality of elastic members in contact with the inner surface of the stent at a distal portion of the stent and a plurality of elastic members in contact with the inner surface of the stent at a proximal portion of the stent, the plurality of elastic members in contact with the inner surface of the stent at the proximal portion of the stent positioned being positioned closer to one another than the plurality of elastic members in contact with the inner surface of the stent at the distal portion of the stent.

4. The stent delivery system according to claim 2, wherein all of the elastic members contact the inner surface of the stent at a proximal portion of the stent, and none of the elastic members contact the inner surface of the stent at a distal portion of the stent.

5. A stent delivery system comprising:
   a stent having a hollow shape, compressed toward a center axis of the stent during insertion into a living body, and restorable to its pre-compression shape by expanding outward when indwelled in the living body;
   an inner tube body having a guide wire lumen configured to receive a guide to assist guiding movement of the stent delivery system in the living body;
   a stent-containing tube body having a distal portion containing the stent, the stent covering a distal portion of the inner tube body, the stent being dischargeable from the stent-containing tube body by moving the stent-containing tube body proximally relative to the inner tube body;
   the inner tube body including an elastic member disposed at a position at least within a proximal portion of the stent, the elastic member being a wire coil comprised of a plurality of windings, at least one of the windings being a fixation section contacting the outer surface of the inner tube body to fix the elastic member to the inner tube body and at least an other of the windings being an elastic section contacting the inner surface of the stent to press the stent in a direction toward the stent-containing tube body, at least a part of the elastic section contacting the inner surface of the stent also being radially outwardly spaced from the outer surface of the inner tube body; and
   the stent is clamped between the elastic member and the stent-containing tube body, and is slidable relative to the stent-containing tube body.

6. The stent delivery system according to claim 5, wherein:
   the stent has a distal portion extending toward a distal end of the stent-containing tube body and a proximal portion extending toward a proximal end of the stent-containing tube body;
   the stent does not have any bent portion which protrudes toward the proximal end and is unconnected to another strut of the stent, other than the proximal portion; and
   by moving the stent-containing tube body distally relative to the inner tube body after exposing a distal end portion of the stent from the stent-containing tube body, the exposed portion of the stent is once again positionable in the stent-containing tube body.

7. The stent delivery system according to claim 5, wherein the elastic section is deformable and is configured to incline in a proximal direction when pulling the stent-containing tube body to move proximally relative to the inner tube body, and to incline in a distal direction when pushing the stent-containing tube body to move distally relative to the inner tube body.

8. The stent delivery system according to claim 5, wherein at least the elastic section of the wire coil is inclined in a proximal direction or in a distal direction.

9. The stent delivery system according to claim 5, wherein a plurality of the elastic members are fixed to the inner tube body.

10. The stent delivery system according to claim 5, wherein a plurality of the elastic members are positioned to press against the stent in a region ranging from a central portion of the stent to the proximal portion of the stent, and wherein there are no elastic members pressing against the stent in a region ranging from the central portion of the stent to a distal end of the stent.

11. The stent delivery system according to claim 5, wherein a plurality of the elastic members are provided in an area ranging from a distal portion of the stent to the proximal portion of the stent.

12. The stent delivery system according to claim 5, wherein the elastic member presses at least a part of an inner surface of the stent by contacting the inner surface of the stent.

13. The stent delivery system according to claim 5, wherein:
   a plurality of the elastic members are provided and are spaced apart from one another;
   the elastic members press at least a part of an inner surface of the stent by contacting the inner surface of the stent; and
   parts of the stent pressed by the elastic members are arranged substantially rectilinearly along an axial direction of the stent.

14. The stent delivery system according to claim 5, wherein:
   a plurality of the elastic members are provided and are spaced apart from one another;
   the elastic members press at least a part of an inner surface of the stent by contacting the inner surface of the stent; and
   parts of the stent which are pressed by adjacent ones of the elastic members are different as viewed along an axial direction of the stent.

15. The stent delivery system according to claim 5, wherein:
   a plurality of the elastic members are provided and are spaced apart from one another;
   the elastic members press at least a part of an inner surface of the stent by contacting the inner surface of the stent; and
   parts of the stent which are pressed by the elastic members are arranged zigzag along an axial direction of the stent.

16. The stent delivery system according to claim 5, wherein the elastic member further comprises:
   a starting end fixation section fixed to the inner tube body and an opposite end either fixed to the inner tube body or forming a free end; and
   a spirally shaped stent-pressing elastic section between the starting end fixation section and the opposite end, the spirally shaped stent-pressing elastic section extending over a predetermined length along an axial direction of the stent.

17. The stent delivery system according to claim 5, wherein the elastic member comprises:
   a starting end fixation section fixed to the inner tube body and an opposite end either fixed to the inner tube body or forming a free end; and
   a leaf spring-configured stent-pressing elastic section between the starting end fixation section and the opposite end, the leaf spring-configured stent-pressing elastic section extending over a predetermined length along an axial direction of the stent and projecting at a central portion of the leaf spring-configured stent-pressing elastic section.

18. The stent delivery system according to claim 5, wherein the inner tube body comprises a distal-side tube having the guide wire lumen, and an inner tube main body having a distal portion fixed to a proximal end of the distal-side tube.

* * * * *